United States Patent [19]

Venkatachalam

[11] Patent Number: 5,724,967

[45] Date of Patent: Mar. 10, 1998

[54] NOISE REDUCTION APPARATUS FOR LOW LEVEL ANALOG SIGNALS

[75] Inventor: Kalpathi Lakshminarayanan Venkatachalam, Palo Alto, Calif.

[73] Assignee: Nellcor Puritan Bennett Incorporated, Pleasanton, Calif.

[21] Appl. No.: 590,269

[22] Filed: Nov. 21, 1995

[51] Int. Cl.⁶ .................................................. A61B 5/00
[52] U.S. Cl. .................. 128/633; 250/214 R; 128/696; 128/902
[58] Field of Search ...................... 128/630, 633, 128/902, 635, 639, 696, 733, 734; 250/214 R, 214.1, 214 A, 214 C

[56] References Cited

U.S. PATENT DOCUMENTS

| | | | |
|---|---|---|---|
| 3,559,193 | 1/1971 | Savaglio et al. | 128/902 |
| 4,194,511 | 3/1980 | Feldman | 128/902 |
| 4,243,045 | 1/1981 | Maas | 128/696 |
| 4,991,580 | 2/1991 | Moore | 128/696 |
| 5,217,013 | 6/1993 | Lewis et al. | 128/633 |
| 5,427,111 | 6/1995 | Traub et al. | 128/902 |
| 5,467,034 | 11/1995 | Manlove et al. | 327/63 |
| 5,517,035 | 5/1996 | Krijntjes | 250/214 A |

*Primary Examiner*—Jennifer Bahr
*Assistant Examiner*—Eric F. Winakur
*Attorney, Agent, or Firm*—Nawrocki, Rooney & Sivertson

[57] ABSTRACT

Pairs of signal input leads with a low level signal imposed across them usually have noise induced by stray coupling capacitance which is typically unequal. This results in an unfavorable signal to noise ratio. Adding enough capacitance to the lead having the least capacitance, thereby equalizing the coupling capacitances to the noise services thereof, tends to reduces the noise effect considerably. This is accomplished by changing the relative sizes of the anode and/or cathode of a corresponding sensor device. The noise effect is further reduced by a negative feedback process which comprises extracting the induced noise component from the leads, inverting the noise component, and coupling the inverted noise component back to the input leads.

7 Claims, 7 Drawing Sheets

NOISE REDUCTION APPARATUS FOR LOW LEVEL ANALOG SIGNALS

FIELD OF THE INVENTION

The present invention relates to improvements to the signal-to-noise ratio of low level analog signals in the presence of interfering signals.

BACKGROUND OF THE INVENTION

The use of low level analog signals in certain electrical applications has become increasingly common in recent years. This is particularly true in the medical device field. One such example is the use of low level analog signals in low power applications, such as cardiac pacemakers or the like, where a battery must power the device for an extended period of time. Another example of the use of low level analog signals is in an oximeter application, where light is provided through a body part and detected by a photodetector. The signal detected by the photodetector is greatly attenuated by transmission through the body part, and thus, the photodetector may only provide a low level analog signal to a processing circuit. It is recognized that these are only exemplary applications for low level analog signals, and that many other applications exist, including applications outside of the medical field.

A common problem when using low level analog signals is that even relatively low levels of external noise may mask out the low level signal, and thus, inhibit the detection of the signal by a receiving portion of the circuit. example, unequal capacitive coupling on each electrode of a sensor may provide a considerable amount of the noise to a corresponding amplifier. Accordingly, because of the low amplitude of the low level signal, the signal-to-noise ratio may be prohibitively small for reliable circuit operation. This is typical of the type of signal provided by a variety of analog sensor means, including the photosensor means of the oximeter application described above.

A common solution to this problem is to enclose the sensitive circuitry within a shielded box or the like to reduce the external noise that reaches the sensor and/or circuit. While this solution may provide some benefit, impedance between the shielded box and the internal nodes of the sensor and/or circuit may itself cause noise within the sensor and/or circuit. Further, the shielded box approach may be too bulky or costly for a given application.

An alternative approach is suggested in U.S. Pat. No. 4,523,090 issued to Wagner. Wagner suggests providing optional variable capacitors to balance the input capacitance of a detector amplifier to enhance alternating current common mode rejection. A limitation of Wagner is that discrete capacitors, and especially variable discrete capacitors, may be more costly and bulky than the shielded box approach discussed above. Thus, Wagner's approach may not lend itself to many applications, including an oximeter application.

Another alternative approach is suggested in U.S. Pat. No. 4,063,167, issued to Duly. Duly is concerned with detecting a change in capacitance on a probe, wherein the probe and the corresponding processing circuitry are connected via a shielded cable having two leads. Duly suggests providing a first and second battery between the two leads of the cable, and providing a midpoint voltage to the shield of the two lead cable, thereby balancing the voltage on each lead with respect to ground. By providing a voltage to each lead with respect to ground, it is known that the low level noise induced thereon will be less. Duly appears to use this principle to minimized common mode noise within the cable. A limitation of Duly is that the two leads must be operated at a positive voltage, which may be unacceptable in some applications. Further, the two battery sources may be more costly and bulky than the shielded box approach or the Wagner approach discussed above. Thus, Duly's approach may not lend itself to many applications, including an oximeter application.

SUMMARY OF THE INVENTION

The instant invention provides an improvement to the signal-to-noise ratio of low level analog signals by increasing the immunity thereof to external noise. One embodiment of the present invention includes a sensor device having a first electrode and a second electrode, wherein the first and second electrodes are coupled to a differential amplifier. The signals generated by the sensor device on the first and second electrodes are typically low level signals.

In accordance with the present invention, one means for increasing the noise immunity on the first and second electrodes is to equalize the capacitance on each electrode. This may be accomplished by any number of means, including designing each electrode within the sensor device to have a cross-sectional area such that the capacitances from each electrode to the noise source are substantially equal. By equalizing the capacitance on each electrode to the noise source, the noise on each electrode may be substantially the same and may be rejected by a differential amplifier, particularly since most modern differential amplifiers have a high common-mode rejection ratio.

Another means for increasing the noise immunity is to generate an inverted noise signal derived from the noise appearing on the first and second electrodes. The inverted noise signal may be coupled back to a shield or the like on or around the sensor device. Thus, noise that is present on the shield of the sensor device may be effectively canceled by the inverted noise signal. Both of these approaches result in an increased signal-to-noise ratio on the internal nodes therein. It is contemplated that the advantages and benefits of the present invention are not limited to the exemplary embodiments described above, but rather may be applicable to any electrical apparatus which utilizes a low level analog signal that is susceptible to noise.

In another related embodiment, the present invention is used to improve the signal-to-noise ratio in an oximetry apparatus. In the oximetry apparatus, light at two or more different wavelengths, usually generated using Light Emitting Diodes (LEDs), is allowed to pass through a capillary bed within the body, and sensed by one or more photodetectors. The wavelengths are selected such that one of the two or more different wavelengths is more strongly absorbed by red blood cells that contain oxygen than is a second of the two or more wavelengths. The differential absorption of the different wavelengths is used to compute the oxygen saturation in the blood.

It is recognized that the amount of light generated by a typical LED is quite low and the attenuation of light transmitted through a finger or the like is quite high, thereby resulting in a very low light level that must be detected by the photodetector(s). Accordingly, a very low level current signal is produced by the photodetector(s), which must be detected and processed by supporting circuitry. In many cases, these low level current signals are partially or even totally masked by noise coupled therein by inherent coupling capacitance between the patient and the photodetector. This problem can be partially addressed by providing a perforated Faraday cage over the photodetector. Further a current-to-voltage differential amplifier may be used to amplify the signals and assist in rejecting some of the common-mode capacitively coupled noise. While this may produce an improved signal, noise coupled by unequal coupling capacitance between the Faraday cage and the electrodes of the photodetector may result in asymmetrically induced noise, which cannot be rejected using a differential amplifier.

In accordance with the present invention, noise at the output of the differential amplifier may be greatly reduced by adding capacitance to the electrode of the photodetector having the smaller total capacitance to the patient, or Faraday cage if provided, until the two electrodes have substantially equal total capacitances. This can be accomplished in the oximetry apparatus by adjusting the area of the cathode and/or anode of the photodetector sensor chip, such that the total capacitance of each is substantially equal to the other. It has been found that when the capacitances are matched to within 0.1 picofarads by adjusting the areas as described above, the coupled noise is very nearly identical at the two inputs of the differential amplifier and can be rejected by the common-mode rejection thereof. Thus, it has been found that by matching the capacitance as described above, the need and associated cost of a Faraday cage around the detector may be obviated, or enhanced immunity may be achieved when used in conjunction with a Faraday cage.

Further improvements may be achieved by coupling the anode and cathode of the photodetector to a differential I/V converter with common-mode drive. The differential I/V converter of the present invention produces two equal but opposite low level voltage signals centered about ground, with a residual noise component intermixed therewith. The absolute value of the difference between the two equal and opposite low level voltage signals is proportional to the photocurrent produced by the photodetector. The two equal and opposite low level voltage signals may then be summed together via a summation means, thus effectively canceling out the two equal and opposite low level voltage signals. The only remaining component on the output of the summation means is the pure residual noise signal. The pure residual noise signal may then be inverted and provided back to the Faraday cage (if used) or a metal trap attached to the patient. This, in effect, cancels out the original noise signal, and thus, greatly improves the system's immunity to external coupled noise.

BRIEF DESCRIPTION OF THE DRAWINGS

The objects and many of the attendant advantages of the present invention will be readily appreciated as it becomes better understood in connection with the accompanying drawings, in which like reference numerals designate like parts throughout the figures thereof and wherein.

DETAILED DESCRIPTION OF THE PREFERRED EMBODIMENTS

Figure 1:
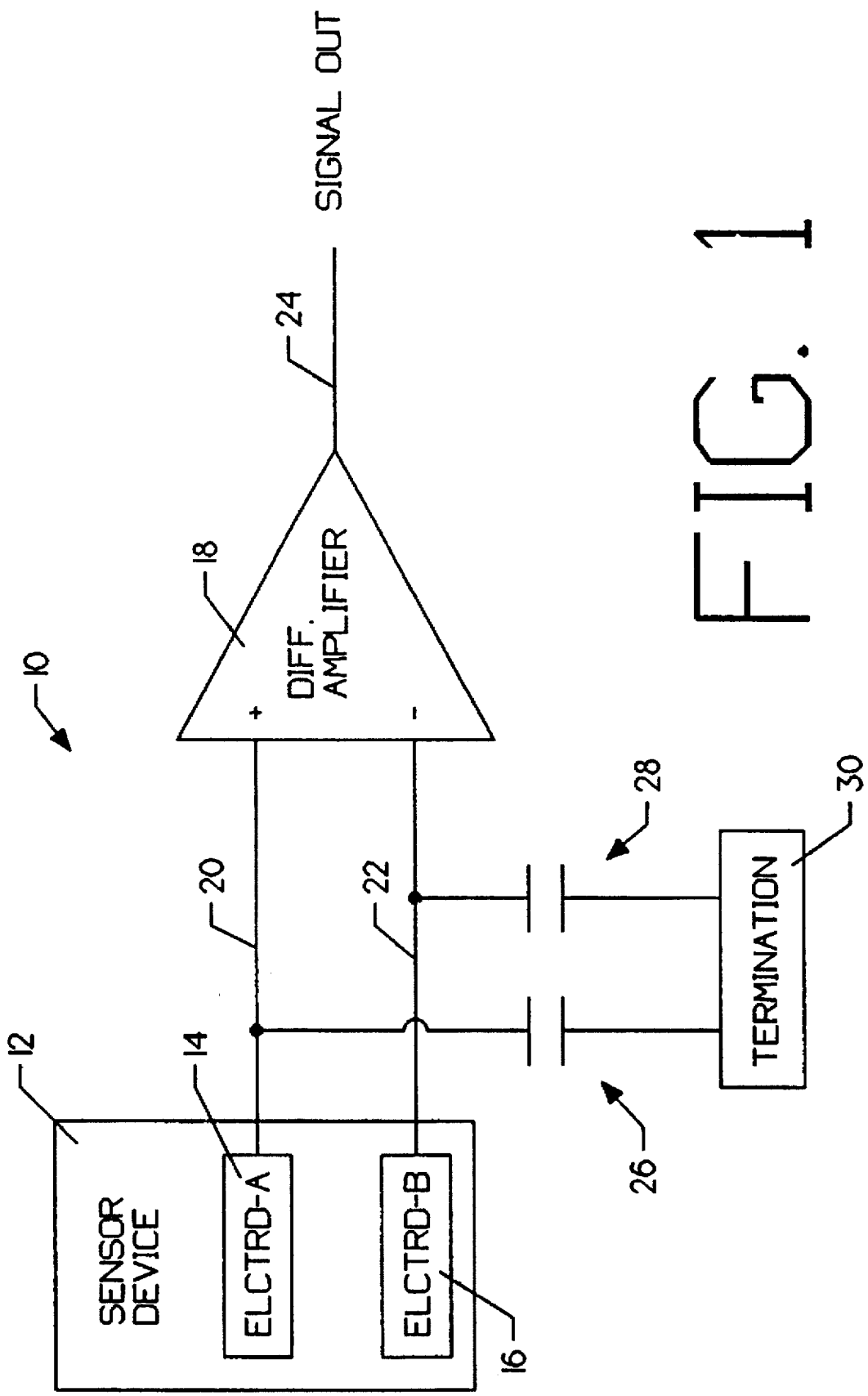
FIG. 1 is a schematic diagram of a first illustrative embodiment of the present invention.

FIG. 1 is a schematic diagram of a first illustrative embodiment of the present invention. The diagram is generally shown at 10. A sensor device 12 having electrodes 14 and 16 is provided, wherein electrodes 14 and 16 are coupled to a differential amplifier 18 via interfaces 20, and 22, respectively. The signals generated by the sensor device 12 and provided on electrodes 14 and 16 are typically low level signals as is described in further detail below.

A common problem when using low level analog signals, on for example interfaces 20 and 22, is that even relatively low levels of external noise may mask out the low level signal, and thus inhibit the detection of the signal by a receiving portion of the circuit. That is, because of the low amplitude of the low level signal, the signal-to-noise ratio may be prohibitively small for reliable circuit operation.

One of the most common ways that unwanted noise may be coupled onto interfaces 20 and 22 is through stray capacitance. Referring to FIG. 1, capacitance 26 represents the unwanted (or stray) coupling capacitance from a termination point 30 to interface 20. A typical source of the unwanted capacitance may be a Faraday cage (not shown) that is placed around sensor device 12 and/or interface 20. If no Faraday cage is provided, there may be unwanted capacitance between electrode 14 of sensor device 12 and literally any conductive object that is near sensor device 12, like the sensor device's package (not shown) or any other object in close proximity thereto. Similarly, capacitance 28 represents the unwanted coupling capacitance from termination point 30 to interface 22. Typical sources of capacitance 28 may be the same as described above with reference to capacitance 26.

A common solution for reducing unwanted noise on internal nodes within a grounded circuit is to enclose the sensitive circuitry within a shielded box or the like. While this solution may provide some benefit, impedance between the imperfectly grounded shielded box itself and the internal nodes of the circuit may cause noise within the circuit. Further, the shielded box approach may be too bulky or costly for a given application.

The present invention provides an improvement to the signal-to-noise ratio of low level analog signals by increasing the immunity thereof to external noise. In accordance with the present invention, one means for increasing the noise immunity on electrodes 14 and 16 is to equalize the unwanted capacitance on each electrode and provide the result to a differential amplifier 18. This solution recognizes that common-mode noise is not inherently harmful to circuit performance, provided that the result is fed into a differential amplifier with a high common-mode rejection ratio. It is only when unequal capacitive coupling is present at the inputs of differential amplifier 18 that a considerable amount of the noise may appear on the amplifier output 24.

Thus, in accordance with one illustrative embodiment of the present invention, it is contemplated that unwanted capacitances may be balanced between electrodes 14 and 16. This may be accomplished by any number of means, but in a preferred mode each electrode 14 and 16 within the sensor device 12 may be designed such that the total unwanted capacitance on each electrode 14 and 16 is substantially the same. Since the capacitance for a parallel plate capacitor is given as $C=\epsilon A/d$, where s is permittivity, A is the cross sectional area, and d is the separation distance, the unwanted capacitance may be controlled by adjusting the areas of electrodes 14 and 16. Accordingly, the noise on each electrode may be substantially the same and may be rejected by differential amplifier 18, particularly since most modern differential amplifiers have a high common-mode rejection ratio.

It is recognized that capacitors 26 and 28 are only illustrative, and that the present invention may be used to balance any unwanted impedance to provide an increased noise immunity to a corresponding low level signal as described above.

Figure 2:
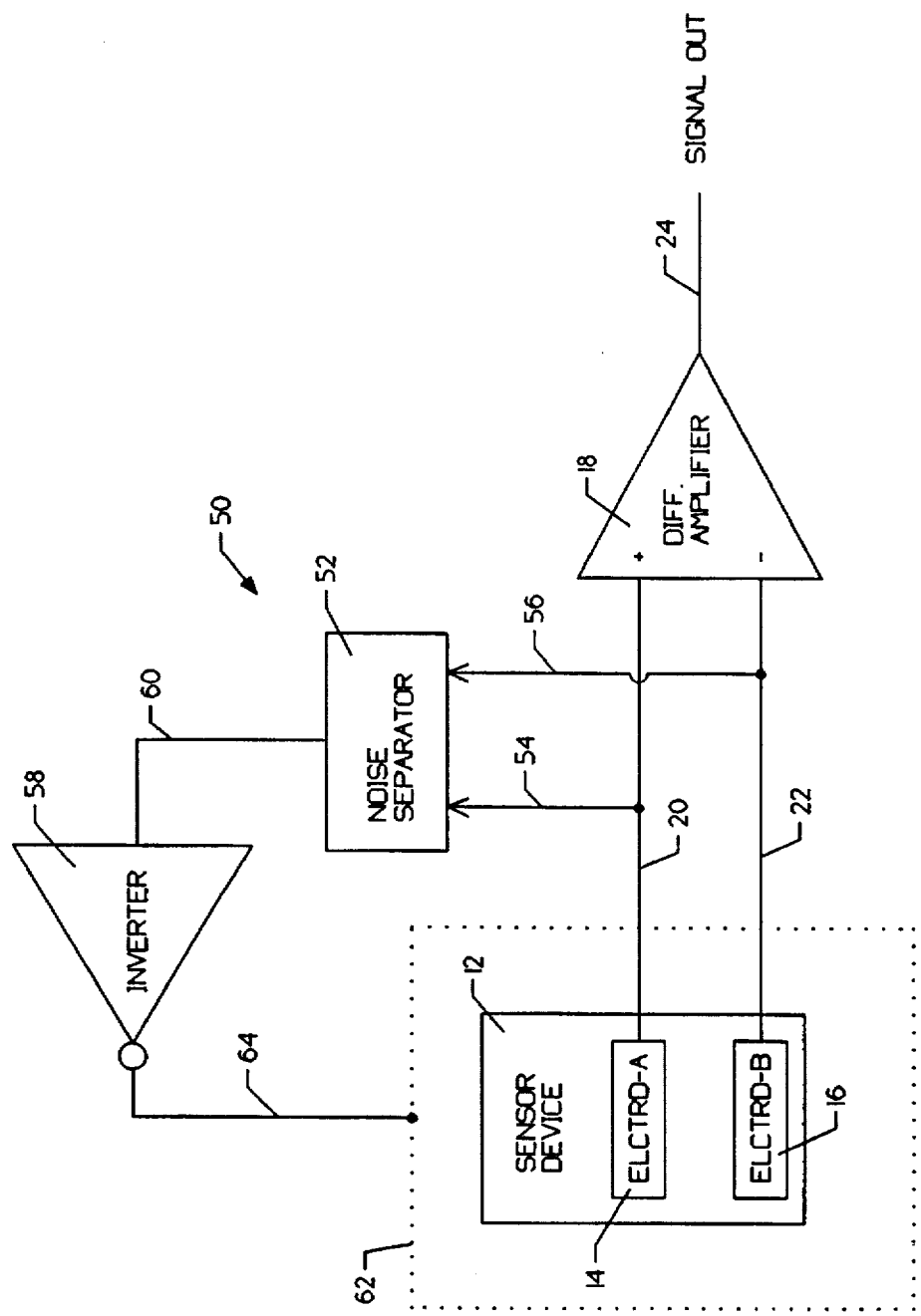
FIG. 2 is a schematic diagram of a second illustrative embodiment of the present invention.

FIG. 2 is a diagram of a second illustrative embodiment of the present invention. The diagram is generally shown at 50. In this embodiment, rather than balancing the impedance between the electrodes and a shield 62 or patient (not shown), the noise immunity may be improved by generating an inverted noise signal derived from the noise appearing on electrodes 14 and 16. In accordance therewith, a noise separator 52 may separate the noise from the signals on interfaces 20 and 22. Noise separator 52 may then provide the noise signal to an inverter 58 via interface 60. Inverter 58 may invert the noise signal, and provide the inverted noise signal back to shield 62 or the patient via interface 64.

In this configuration, unwanted noise or interference that is present on shield 62 or the patient may be effectively canceled by the inverted noise signal. This may substantially reduce the noise that is coupled into the sensor device 12 via unwanted impedance that may exist between shield 62 and sensor device 12. Although it is not deemed necessary, it is contemplated that this embodiment may be used in conjunction with the embodiment described with reference to FIG. 1 to achieve even further noise immunity.

Both of the above referenced approaches may result in an increased signal-to-noise ratio on the internal nodes of sensor device 12. It is contemplated, however, that the advantages and benefits of the present invention are not limited to the illustrative embodiments described above, but rather are deemed applicable to any electrical apparatus which utilizes a low level analog signal that may be susceptible to noise.

Figure 3:
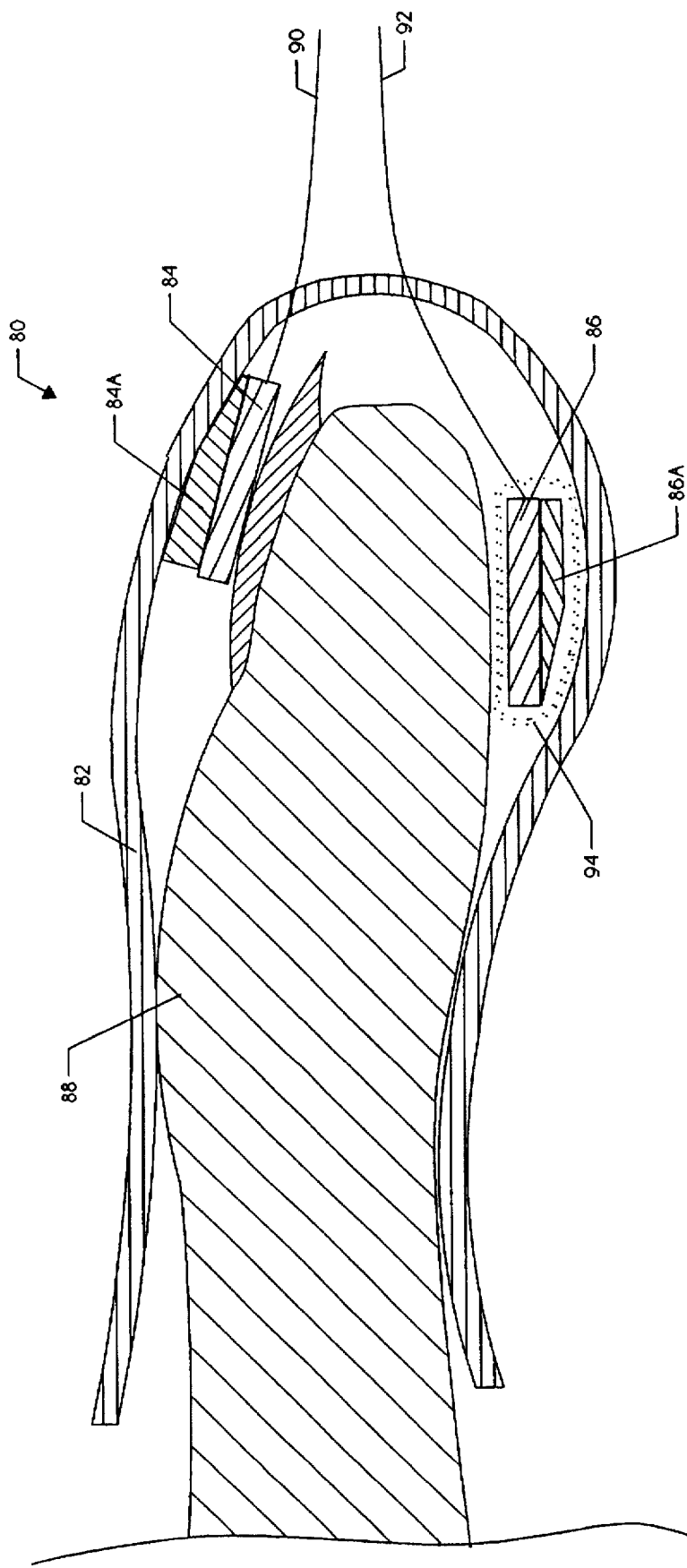
FIG. 3 is a cross sectional side view of an oximeter sensor.

FIG. 3 is a cross sectional side view of an oximeter sensor 80. Oximetry sensor 80 comprises an attachment clip 82 which supports LED pair 84 and photodetector 86 on opposite sides of finger 88. Supporting members 84A and 86A are attached to clip 82 and to LED pair 84 and photodetector 86, respectively, by adhesive or the like to secure the LEDs and photodetector to the clip. Cables 90 and 92 provide the electrical connections for LED pair 84 and photodetector 86, respectively, from sensor 80 to the remainder of the apparatus (not shown). This figure illustrates the path that the light emitted by LED pair 84 must take through the finger 88 to photodetector 16 with resulting attenuation. It is contemplated that the oximeter apparatus of the present invention may be constructed in accordance with U.S. Pat. No. 4,700,708, issued on Oct. 20, 1987 to New. Jr. et al., which is hereby incorporated by reference.

In the illustrative embodiment, LED pair 84 may emit light at two or more different wavelengths wherein each wavelength is allowed to pass through finger 88, and may be detected by photodetector 86. A time division multiplexed algorithm may be used such that photodetector 86 may detect the intensity of each of the two or more different wavelengths over a given time period. The wavelengths that are emitted by LED pair 84 may be selected such that one of the two or more different wavelengths is more strongly absorbed by red blood cells that contain oxygen than is a second of the two or more wavelengths. The differential absorption of the different wavelengths is used to compute the oxygen saturation in the blood.

It is recognized that the amount of light generated by LED pair 84 may be quite low and the attenuation of light transmitted through finger 88 or the like may be quite high, thereby providing a very low light level to photodetector 86. Accordingly, a very low level current signal from photodetector 86 may be provided to a corresponding processing circuit (not shown). Further, the low level signals may be partially or totally masked by noise pickup coupled from the patient's finger 88 to the electrodes of photodetector 86.

It is contemplated that a perforated Faraday cage 94 may be provided over the photodetector as shown. It is recognized that Faraday cage 94 may provide some benefit. However, impedance between Faraday cage 94 and the internal nodes of photodetector 86 may cause unwanted noise within photodetector 86. Further, Faraday cage 94 may be too bulky or expensive for a given application.

Figure 4A:
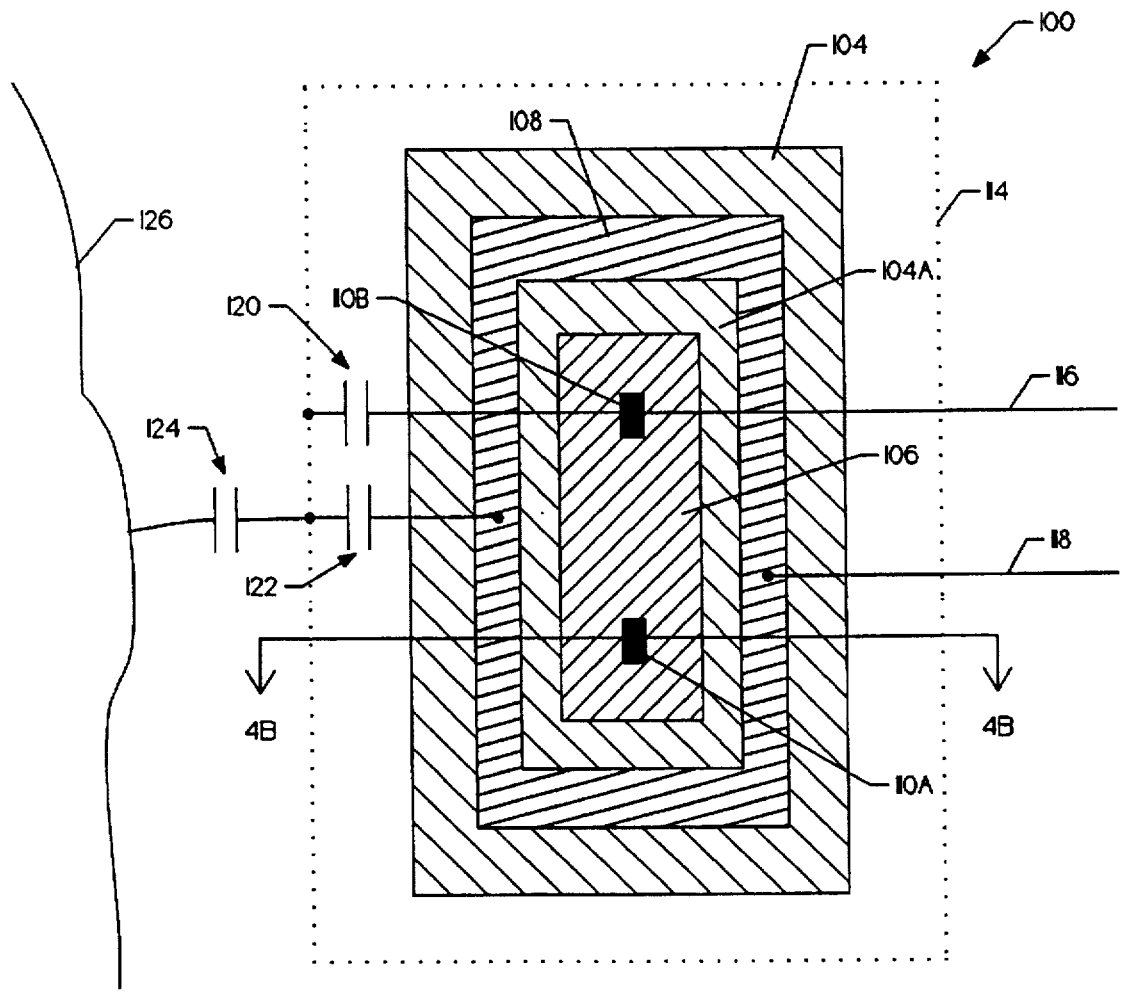
FIG. 4A is a top view of a photodetector chip showing stray capacitance to a Faraday cage and to a patient's finger.
Figure 4B:
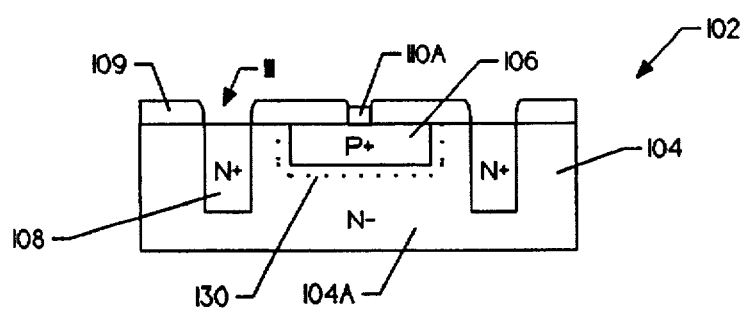
FIG. 4B is a cross sectional side view of the photodetector chip of FIG. 4A, taken along line 4B—4B.

FIG. 4A is a top view of a photodetector chip showing stray capacitance to a Faraday cage and to a patient's finger. FIG. 4B is a cross sectional side view of the photodetector chip of FIG. 4A, taken along line 4B—4B. The photodetector may be used to detect wavelengths of light provided by an LED pair as described with reference to FIG. 3. It is contemplated that the photodetector chip may be a 3 mm$^2$ (large) photodiode, available from Centronic Inc.

Generally, the photodetector chip comprises a photodiode. The photodiode comprises a PN junction with an anode 106 and a cathode 108. The anode 106 and cathode 108 may be implanted into a N− type tub 104 as shown in FIG. 4B. Anode 106 may comprise a relatively thin P+ implant such that the resulting P+N− junction is very near the surface of the photodiode chip. This is important in photosensor application because the light may only penetrate the surface of the photodiode a short distance. Cathode 108 may comprise an N+ implant that extends circumferentially around the P+ anode implant as shown in FIG. 4A. It is recognized that the N+ cathode implant may abut the P+ anode implant with little or no effect on the characteristics of the diode. Cathode 108 is electrically connected to the N− tub 104, as both the N+ cathode 108 and the N− tub 104 are N type implants. Thus, the N− tub functions as part of the cathode of the diode.

The anode 106 may have a number of contacts provided thereon. In a preferred embodiment, two metal contacts 110A and 110B are provided. This allows the photodetector chip to be oriented either in an "UP" position or "DOWN" position within a photodetector package and still have the same interconnection positions. Further, the photodetector chip may be tested using one of the metal contacts, which commonly leaves a probe mark thereon, while leaving the other metal contact clean to form a wire bond or the like to the photodetector package. This configuration may provide added reliability to the system.

In a preferred embodiment, the metal contacts 110A and 110B comprise a minimum 0.25 mm diameter gold or aluminum pad, compatible with gold ball thermosonic wire bond or ultrasonic aluminum wire bond. In addition, cathode 108 may have a gold or silver film deposited on the surface thereof, which is preferably compatible with conductive epoxy die attach.

With reference to FIG. 4B, the top surface of the photodiode may have a silicide layer 109 deposited thereon to provide insulation and protection to the photodiode substrate. The silicide layer 109 may be etched using a standard etching process to provide openings therein for metal contacts 110A and 110B, and the cathode contact area 111.

Pursuant to semiconductor physics principles, it is known that a space-charge region exists at the junction between the P+ implant 106 and the N– tub region 104A (or cathode) as shown at 130. The significance of the space-charge region 130, as it relates to the operation of a typical photodiode, is discussed with reference to FIG. 4C.

A body part is shown at 126 and a Faraday cage is shown surrounding the photodetector at 114. There may be unwanted capacitance between Faraday cage 114 and anode 106 as shown at 120. Further, there may be unwanted capacitance between Faraday cage 114 and cathode 108 as shown at 122. Finally, there may be unwanted capacitance between Faraday cage 114 and body part 126 as shown at 124. If Faraday cage 114 is not provided, there may be unwanted capacitance between body part 126 and anode 106, and between body part 126 and cathode 108. The present invention reduces the effects of these unwanted capacitances on circuit operation.

It is contemplated that the concentrations and polarities of the photodiode implants as described above may be varied and or reversed and still provide the same general function.

Figure 4C:
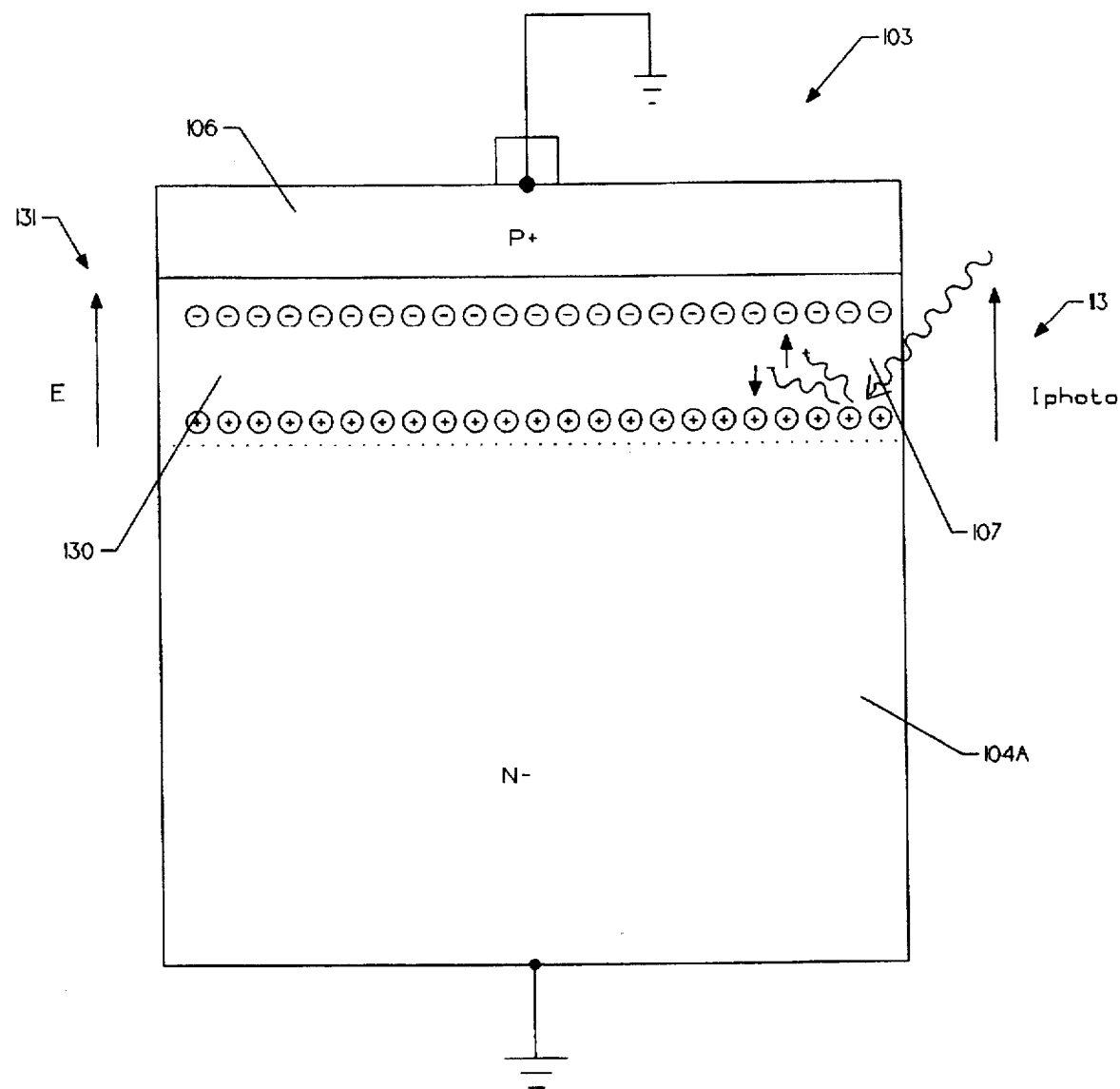
FIG. 4C is an expanded cross sectional side view of the space-charge region of FIG. 4B.

FIG. 4C is an expanded cross sectional side view of the space-charge region 130 of FIG. 4B. The diagram is generally shown at 103. To properly describe the operation of the schematic diagram shown in FIG. 6, a general description of the operation of photodiode 100 is presented. As indicated with reference to FIG. 4B, a space charge region 130 exists between the P+ implant of anode 106 and the N– implant of cathode 104A. In the space charge region 130, trapped holes are uncovered in the region where the N– implant overlaps space charge region 130. Similarly, trapped electrons are uncovered in the region where the P+ implant overlaps space charge region 130. This results in an electric field 131 extending from the uncovered holes to the uncovered electrons as shown.

When the photodiode is exposed to photons (or light), the photons enter the space charge region 130 and may collide with an atom therein. A certain portion of these collisions cause an electron-hole pair to be released into the space charge region as shown at 107. The electric field 131 causes the released electrons to flow toward the N– implanted cathode region 104A. Similarly, the electric field 131 causes the released holes to flow toward the P+ implanted anode 106. The net result is a photocurrent 113 which flows from the cathode 104A to the anode 106. This current flows as a result of the electric field 131 that is generated by space-charge region 130, and does not require an external bias the diode. This allows the photodiode to be operated in a zero bias mode.

In a typical photodetector application, the photodiode is operated in the zero bias mode and the photocurrent flows from the cathode to the anode. That is, both the anode 106 and the cathode 104A are held substantially at ground as shown in FIG. 4C, and the photocurrent flows from the cathode to the anode and into a current detection circuit (not shown).

In the zero bias mode, the photodiode generates a current that is substantially linear with the intensity of light exposure, thereby making the zero bias mode desirable for sensor applications. In contrast, a voltage measurement mode is less desirable because the photodiode voltage as a function of light intensity is non-linear.

Figure 5:
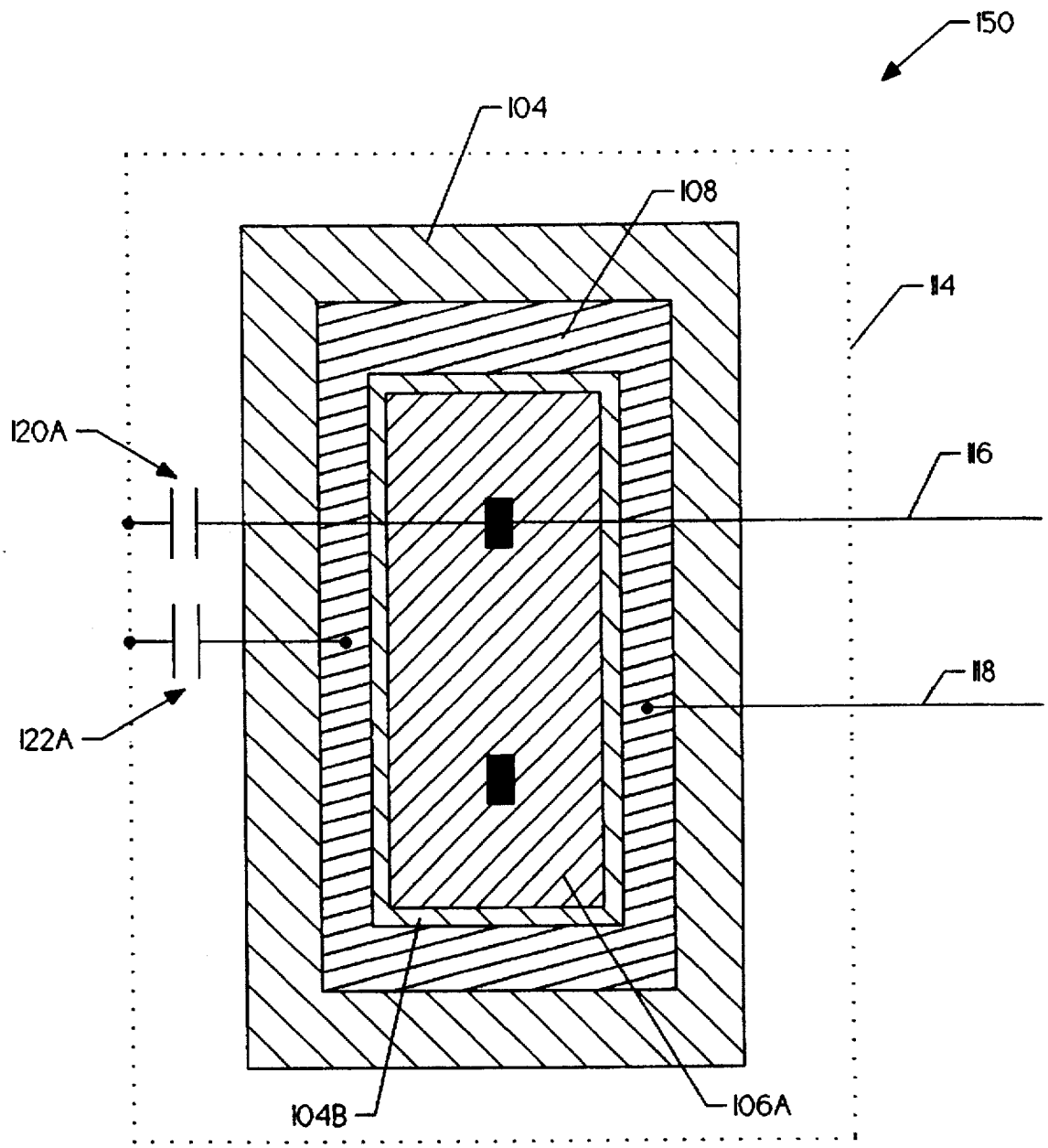
FIG. 5 is a top view of a photodetector chip in accordance with the present invention, wherein the anode area has been enlarged to balance the stray capacitance to the anode and cathode from the Faraday cage.

FIG. 5 is a top view of a photodetector chip in accordance with the present invention, wherein the anode area 106A has been enlarged to balance the stray capacitance of anode 106A and cathode 108 from Faraday cage 114.

Capacitors 120A and 122A represent the stray capacitance between Faraday cage 114, and anode 106A and cathode 108, respectively. Leads 118 and 116 are connected to cathode 108 and anode 106A, respectively, and are the photosensor output leads.

The total capacitance, including stray capacitance 122A, from Faraday cage 114 to cathode 108 is made equal to the total capacitance, including stray capacitance 120A, from the Faraday cage 114 to anode 106A. This is accomplished by first measuring the stray capacitance value of stray capacitances 120A and 122A. After the value of typical capacitances has been determined, these values are averaged to obtain a representative total capacitance for each. The smallest total capacitance value to either the cathode 108 or the anode 106A is then increased an amount equal to their difference by increasing the size of that implant area in the manufacturing process. It is also recognized that the larger of the total stray capacitance values may be decreased an amount equal to their difference and still be within the scope of the present invention.

In the exemplary embodiment, the total area of the anode 106A has been increased from that shown in FIG. 4A. It has been foul if the difference in magnitude of the total capacitance of the two input leads is made less than 0.1 picofarads, the common mode rejection of noise induced by stray capacitance is greatly improved.

It is contemplated that Faraday cage 114 may not be provided. In this case, the stray capacitances 120A and 122A represent capacitances from anode 106A and cathode 108, respectively, to a patient or the like. The stray capacitance values may be determined by placing a clip 82 on a finger, as shown in FIG. 3, and then measuring the total capacitances between finger 88, and anode 106A and cathode 108, respectively, using suitable apparatus. After the value of typical stray capacitances for a number of subjects has been determined, these values may be averaged to obtain a representative total capacitance for each. The smaller of the total values to either the cathode 108 or the anode 106A is then increased by an amount equal to their difference as described above. It is also recognized that the larger of the total stray capacitance values may be decreased an amount equal to their difference and still be within the scope of the present invention.

Figure 6:
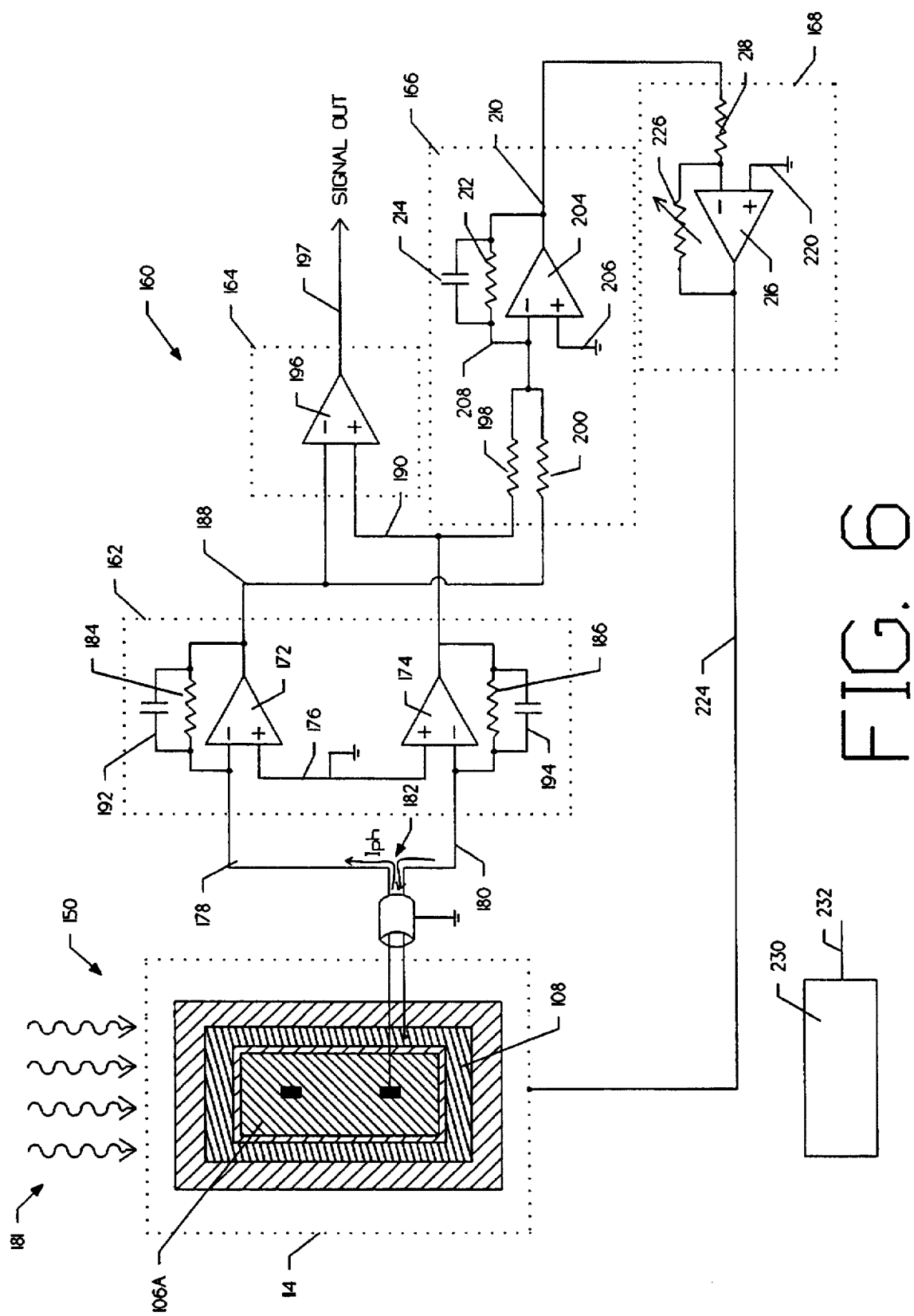
FIG. 6 is a circuit diagram showing a preferred embodiment of the present invention, including means for generating an inverted noise signal and for feeding the inverted noise signal back to a Faraday cage that surrounding a corresponding photodetector.

FIG. 6 is a circuit diagram showing a preferred embodiment of the present invention, including means for generating an inverted noise signal and for feeding the inverted noise signal back to a Faraday cage or patient. The diagram is generally shown at 160. Generally, the apparatus comprises a photodetector 150, a differential I/V converter 162, a final stage amplifying circuit and differential-to-single ended converter 164, an inverting summation circuit 166, and an inverting circuit 168.

As indicated with reference to FIG. 3, photodetector 150 is placed adjacent to a body part and may detect various wavelengths of light 181 that are emitted from an LED pair located on another side of the body part. The anode 106A of photodetector 150 is coupled to amplifier 172 via interface 178. Similarly, the cathode 108 of photodetector 150 is coupled to amplifier 174 via interface 180.

The positive inputs of amplifiers 172 and 174 are tied to ground via interface 176 as shown. In a preferred embodiment, amplifiers 172 and 174 are operation amplifiers available from Burr Brown as part number OPA2107. A resistor 184 and a capacitor 192 are coupled from the output of amplifier 172 to the negative input thereof. Similarly, a resistor 186 and a capacitor 194 are coupled from the output of amplifier 174 to the negative input thereof. The capacitor resistor parallel combinations are selected to provide a high frequency roll off to attenuate frequencies higher than frequencies of interest. In a preferred mode, resistors 184 and 186 have values of about 249 KΩ and capacitors 192 and 194 have values of about 22 picofarads, thereby resulting in a low pass filter with a cutoff frequency of about 30 KHz.

In the above described configuration, the negative inputs of amplifiers 172 and 174 tend to follow the positive inputs thereof. Since the positive inputs are tied to ground via interface 176, the negative inputs are effectively tied to a "virtual" ground. It is readily apparent that the photodetector 150 is operated in a zero-bias mode, as discussed with reference to FIG. 4C. In this mode, the photocurrent flows from the cathode 108 to the anode 106A thereof, as shown at 182. Further, the photocurrent is substantially linear with light intensity.

Generally, the photocurrent 182 flows from the output of amplifier 174, through resistor 186, photodetector 150, resistor 184, and into the output of amplifier 172. Since the negative inputs of amplifiers 172 and 174 are held at "virtual" ground, the photocurrent generates a positive voltage on the output of amplifier 174, and a negative voltage on the output of amplifier 172. Accordingly, amplifiers 172 and 174 provide a conversion of the photodetector current into a voltage. Since resistors 184 and 186 have the same value, the voltage on the output of amplifier 174 is equal and opposite to the voltage on the output of amplifier 172.

The outputs of amplifiers 172 and 174 are connected to the negative input and positive input, respectively, of amplifier 196 which converts the differential output into a single-ended, ground referenced output. In a preferred embodiment, amplifier 196 is a high accuracy differential amplifier with laser trimmed resistors, and provides a high accuracy output signal. Such an amplifier is available from Burr-Brown as part number INA105.

The outputs of amplifiers 172 and 174 are also connected to one end of identical sized resistors 198 and 200, which have their opposite ends connected to the negative input of amplifier 204. The positive input of amplifier 204 is grounded. Resistor 212 and capacitor 214 are connected in parallel between the output of amplifier 204 and the negative input.

With these connections, amplifier 204 provides an inverted summation of the outputs of amplifiers 172 and 174. Since the voltage on the outputs of amplifiers 172 and 174 are equal and opposite, the sum thereof equals substantially zero. Thus, the inverted summation results in a signal containing only the residual capacitively coupled input noise component on anode 106A and cathode 108. The capacitor resistor parallel combination of resistor 212 and capacitor 214 is selected to provide a high frequency roll off to attenuate frequencies higher than frequencies of interest, although in one embodiment, capacitor 214 is not provided. In a preferred embodiment, resistors 198, 200, and 212 all have values of approximately 10 KΩ. Further, amplifier 204 is preferably part number OPA2107 available from Burr-Brown.

The output of amplifier 204 is also connected to one end of resistor 218 which has the opposite end connected to the negative input of amplifier 216. The positive input of amplifier 216 is grounded. Variable resistor 226 is connected from the output of amplifier 216 to the negative input. Variable resistor 226 provides a means for changing the gain of amplifier 216. In a preferred embodiment, amplifier 216 is part number OPA2107, available from Burr-Brown.

The output of amplifier 216, is an inverted pure residual noise signal on anode 106A and cathode 108. Since the noise signals were first inverted by amplifiers 172 and 174, reinverted and summed by amplifier 204, and inverted again by amplifier 216; the output of amplifier 216 provides the inverted noise signal. This inverted noise signal is electrically connected either to Faraday cage 114 (if provided), or to a metal strap 230 which is connected to a patient. Either of these connections will couple the inverted noise signal back to the patient, which is the source of the original interference.

The value of resistor 218 and variable resistor 226 are selected to provide an inverted noise signal which is of the proper magnitude to effectively cancel the noise signals induced onto anode 106A and cathode 108. Resistor 226 permits adjusting the magnitude of the inverted noise signal that is fed back to the Faraday cage 114 or the patient, until a minimum noise effect is observed. The noise on the output of amplifier 196 can be observed by using an oscilloscope, while adjusting resistor 226 to produce the minimum noise effect. This adjustment is performed while injecting common-mode noise into the sensor via a patient simulator. In a preferred embodiment, the value of resistor 226 is approximately 100 KΩ and the value of resistor 218 is approximately 10 KΩ.

The combination of balancing the size of the total capacitance to the Faraday cage or the patient, and coupling the inverted noise signal back into the Faraday cage or the patient, greatly reduces the effect of capacitance coupled noise on the system. This improvement in signal-to-noise ratio is achieved with a minimum of complexity, and is relatively straight forward in its application. Conventional analog amplifiers, resistors and capacitors are all that are required. This improvement in signal-to-noise ratio is valuable for any apparatus that measures very small analog currents in the presence of interfering signals.

Having thus described the preferred embodiments of the present invention, those of skill in the art will readily appreciate that the teachings found herein may be applied to yet other embodiments within the scope of the claims hereto attached.

What is claimed is:

1. Apparatus for improving the signal-to-noise ratio of an analog signal having a noise component, comprising:

a. a sensor device for providing the analog signal between an anode and a cathode thereof, at least a portion of the noise component of the analog signal being produced by a stray impedance to the anode and a stray impedance to the cathode, said anode and said cathode being sized such that the stray impedance to the anode and the stray impedance to the cathode are substantially balanced;

b. a differential amplifier coupled to said anode and said cathode of said sensor device for amplifying said analog signal, said differential amplifier having a common-mode rejection capability thereby at least partially rejecting the common mode noise component from the analog signal.

2. Apparatus according to claim 1 wherein said sensor device comprises a photodiode and said analog signal is an analog current signal.

3. A method for improving the signal-to-noise ratio of an analog signal having a noise component in a sensor, the sensor having an anode with a cross sectional area and a cathode with a cross sectional area, the noise component being produced by stray impedance coupled to the anode and the cathode, comprising the steps of:

a. balancing the stray capacitance between the anode and the cathode by changing the size of the cross sectional area of the anode with respect to the cross sectional area of the cathode; and b. providing the analog signal to a differential amplifier having a common-mode rejection capability.

4. A method for improving the signal-to-noise ratio of an analog signal having a noise component in a sensor, the sensor having an anode with a cross sectional area and a cathode with a cross sectional area, the noise component being produced by stray impedance coupled to the anode and the cathode, comprising the steps of:

a. balancing the stray capacitance between the anode and the cathode by changing the size of the cross sectional area of the cathode with respect to the cross sectional area of the anode; and b. providing the analog signal to a differential amplifier having a common-mode rejection capability.

5. A for improving the signal-to-noise ratio of an analog signal having a noise component in a sensor, the sensor having an anode with a cross sectional area and a cathode with a cross sectional area, the noise component being produced by stray impedance coupled to the anode and the cathode, comprising the steps of:

a. balancing the stray capacitance between the anode and the cathode by changing the relative sizes of the cross sectional area of the anode and the cross sectional area of the cathode; and b. providing the analog signal to a differential amplifier having a common-mode rejection capability.

6. A method according to claim 5 wherein said sensor is an oximeter sensor.

7. A method according to claim 6 wherein said oximeter sensor comprises a photodiode.

* * * * *